(12) United States Patent
Shinohara et al.

(10) Patent No.: US 9,441,011 B2
(45) Date of Patent: Sep. 13, 2016

(54) METHOD FOR PURIFICATION OF ANTIBODY USING POROUS MEMBRANE HAVING AMINO GROUP AND ALKYL GROUP BOTH BOUND TO GRAFT CHAIN IMMOBILIZED ON POROUS SUBSTRATE

(75) Inventors: Naoyuki Shinohara, Tokyo (JP); Takashi Ishihara, Takasaki (JP); Hironobu Shirataki, Tokyo (JP); Yoshiro Yokoyama, Tokyo (JP)

(73) Assignees: ASAHI KASEI CHEMICALS CORPORATION, Tokyo (JP); ASAHI KASEI MEDICAL CO., LTD., Tokyo (JP)

( * ) Notice: Subject to any disclaimer, the term of this patent is extended or adjusted under 35 U.S.C. 154(b) by 972 days.

(21) Appl. No.: 13/381,129

(22) PCT Filed: Jun. 29, 2010

(86) PCT No.: PCT/JP2010/061031
§ 371 (c)(1),
(2), (4) Date: Jan. 20, 2012

(87) PCT Pub. No.: WO2011/001963
PCT Pub. Date: Jan. 6, 2011

(65) Prior Publication Data
US 2012/0123002 A1    May 17, 2012

(30) Foreign Application Priority Data
Jul. 3, 2009 (JP) .................................. 2009-158421

(51) Int. Cl.
| B01D 71/78 | (2006.01) |
| B01D 71/24 | (2006.01) |
| C07K 1/22 | (2006.01) |
| B01J 47/12 | (2006.01) |
| B01D 67/00 | (2006.01) |
| B01D 69/08 | (2006.01) |

(52) U.S. Cl.
CPC ............. *C07K 1/22* (2013.01); *B01D 67/0093* (2013.01); *B01D 69/08* (2013.01); *B01D 71/78* (2013.01); *B01J 47/12* (2013.01); *B01D 71/24* (2013.01); *B01D 2323/38* (2013.01)

(58) Field of Classification Search
None
See application file for complete search history.

(56) References Cited

U.S. PATENT DOCUMENTS

| 4,720,343 A | 1/1988 | Walch et al. |
| 5,064,866 A | 11/1991 | Toyomoto et al. |
| 5,547,575 A | 8/1996 | Demmer et al. |
| 5,739,316 A | 4/1998 | Beer et al. |
| 6,001,974 A | 12/1999 | Demmer et al. |
| 6,177,548 B1 | 1/2001 | Wan et al. |
| 6,235,892 B1 | 5/2001 | Demmer et al. |
| 6,780,327 B1 | 8/2004 | Wu et al. |
| 6,783,937 B1 | 8/2004 | Hou et al. |
| 2002/0010319 A1 | 1/2002 | Ansaldi et al. |
| 2005/0107594 A1 | 5/2005 | Sun et al. |
| 2005/0272917 A1 | 12/2005 | Jiao et al. |
| 2007/0112178 A1 | 5/2007 | Johansson et al. |
| 2007/0167613 A1 | 7/2007 | Johansson et al. |
| 2007/0259453 A1 | 11/2007 | Engstrand et al. |
| 2009/0050566 A1 | 2/2009 | Kozlov et al. |
| 2010/0228010 A1* | 9/2010 | Shirataki et al. ............ 530/413 |

FOREIGN PATENT DOCUMENTS

| JP | 2-132132 | 5/1990 |
| JP | 2796995 | 7/1998 |
| JP | 11-12300 | 1/1999 |
| JP | 2002-517406 | 6/2002 |
| JP | 2007-532477 | 11/2007 |
| JP | 2008-500972 | 1/2008 |
| JP | 2008-505851 | 2/2008 |
| JP | 2008-517906 | 5/2008 |
| JP | 2009-53191 | 3/2009 |
| JP | 2010-70490 | 4/2010 |
| JP | 2010-158624 | 7/2010 |
| JP | 2010-241761 A | 10/2010 |
| WO | 95/32793 | 12/1995 |
| WO | 00/50160 | 8/2000 |
| WO | 01/40448 | 6/2001 |
| WO | 02/085519 | 10/2002 |
| WO | 2009/054226 | 4/2009 |

OTHER PUBLICATIONS

Japanese Office Action issued with respect to counterpart Japanese Application No. 2009-538030, dated Mar. 14, 2013.
"New Biochemical Experiments Course 1, Protein 1—separation, purification, properties—", Edited by the Japanese Biochemical Society, First edition, First printing, 1990, with English Translation thereof.

(Continued)

*Primary Examiner* — Krishnan S Menon
(74) *Attorney, Agent, or Firm* — Greenblum & Bernstein, P.L.C.

(57) ABSTRACT

A method is disclosed for purifying an antibody monomer, comprising providing a porous membrane comprising a hydrophobic porous substrate, a hydrophilic molecular chain of a different material from that of the porous substrate, immobilized on the surface of pores of the porous substrate, and a side chain of the molecular chain, containing a nitrogen atom to which one to three alkyl groups each having two or three carbon atoms are bonded; passing an antibody solution containing antibody aggregates of dimers or higher-order multimers through the porous membrane to adsorb the antibody aggregates to the porous membrane; and recovering the purified antibody monomer in the passed solution.

7 Claims, No Drawings

(56) References Cited

OTHER PUBLICATIONS

English Translation of International Preliminary Report on Patentability and Written Opinion for International Application No. PCT/JP2010/061031, mailed Feb. 23, 2012.
Platonova, G.A. et al., "Quantitative fast fractionation of a pool of polyclonal antibodies by immunoaffinity membrane chromatography.", J. Chromatgr. A. vol. 852, 1999, pp. 129-140.
Takanobu Sugo et al., "Hoshasen Graft Jugo ni Okeru ko Kinoka Saizensen Saishukai Hoshasen Graft Jugo Gijutsu o ojo shita Shin Sozai no Sosei", Convertech, vol. 33, No. 12, 2005, pp. 34-38.
Search report from PCT/JP2010/061031, mail date is Aug. 3, 2010.
Okamura et al., "Solvent effect on protein binding by polymer brush grafted onto porous membranes", J. Chromatography A, 953, 2002, pp. 101-109.
U.S. Office action issued with respect to U.S. Appl. No. 12/681,189, mail date is Sep. 25, 2012.
Japanese Office Action issued with respect to Japanese Application No. 2011-520924, mail date is Oct. 16, 2013.
Pete Gagnon, "17, Polishing Methods for Monoclonal IgG Purification", Process Scale Bioseparations for the Biopharmaceutical Industry, Taylor & Francis Group, LLC, 2007, pp. 491-505.
Henry R. Charlton et al., "Characterisation of a generic monoclonal antibody harvesting system for adsorption of DNA by depth filters and various membranes," Bioseparation, vol. 8, pp. 281-291, 1999.
International Search Report for PCT/JP2008/067540, mailed Dec. 22, 2008.
International Preliminary Report on Patentability, including the Written Opinion (in English) for PCT/JP2008/067540, mailed Jun. 10, 2010.
Saito K et al., "Radiation-induced graft polymerization is the key to develop high-performance functional materials for protein purification", Radiation Physics and Chemistry, Elsevier Science Publishers BV., Amsterdam, NL, vol. 54, No. 5, XP004161328 , May 1, 1999, pp. 517-525.
Yonedu Shinji et al., "Affinity elution of gelsolin adsorbed onto an anion-exchange porous membrance", Membrane, vol. 30, No. 5, 2005, XP008142475, pp. 269-274.
Hagiwara K et al., "High-performance purification of gelsolin from plasma using anion-exchange porous hollow-fiber mambrane", Journal of Chromatography B: Biomedical Sciences & Applications, Elsevier, Amsterdam, NL, vol. 821, No. 2, XP004974125, Jul. 25, 2005, pp. 153-158.
Kubota N et al., "Module performance of anion-exchange porous hollow-fiber membranes for high-speed protein recovery", Journal of Chromatography, Elsevier Science Publishers B.V.NL, XP004096270, Oct. 10, 1997, pp. 159-165.
Tsuneda S et al., "High-throughput processing of proteins using a porous and tentacle anion-exchange membrane", Journal of Chromatography, Elsevier Science Publishers B.V.NL, vol. 689, No. 2, XP004023269, Jan. 13, 1995, pp. 211-218.
Ito H, "Comparison of 1-typhtophan binding capacity of BSA captured by a polymer brush with that of BSA absorbed onto a gel network", Journal of Chromatography, Elsevier Science Publishers B.V.NL, XP004296297, Aug. 3, 2001, pp. 41-47.
Koguma et al. "Multilayer Binding of Proteins to Polymer Chains Grafted onto Porous Hollow-Fiber Membranes Containing Different Anion-Exchange Group," Biotechnology Progress, 2000, 16: 456-461.
Search report from E.P.O. that issued with respect to patent family member European Patent Application No. 08842007.0, mail date is Sep. 12, 2011.
International Preliminary Report on Patentability, including the Written Opinion (in English) for PCT/JP2010/061031, mailed Feb. 14, 2012.

* cited by examiner

METHOD FOR PURIFICATION OF ANTIBODY USING POROUS MEMBRANE HAVING AMINO GROUP AND ALKYL GROUP BOTH BOUND TO GRAFT CHAIN IMMOBILIZED ON POROUS SUBSTRATE

TECHNICAL FIELD

The present invention relates to a porous membrane having amino and alkyl groups bound to graft chains immobilized on a porous substrate and a method for purifying a protein using the porous membrane.

BACKGROUND ART

In the food and medical fields, methods for efficiently purifying useful proteins are strongly desired. In the biotechnological industry, large-scale purification of proteins has represented an important challenge in recent years. Particularly in the pharmaceutical field, the demand for antibody drugs is rapidly growing; there is a strong desire to establish technologies that make it possible to efficiently produce and purify large amounts of proteins.

Generally, proteins are produced by cell cultures using animal-derived cell lines. In a typical operation to purify a protein from a cell culture, the cell culture is first centrifuged to precipitate and remove turbid components. Then, cell debris having a size of about 1 µm or less that can not be completely removed by the centrifugation are removed by means of size filtering using a microfiltration membrane. Further, the filtrate is subjected to sterilization filtration using a filtration membrane having a maximum pore size of 0.22 µm or less for sterilization to provide a sterilized solution containing a desired protein (a harvest step). Subsequently, using a purification process employing a combination of a plurality of chromatographic techniques including affinity chromatography typically using protein A, the desired protein is separated and purified by removing contaminants such as host cell proteins (HCPs), deoxyribonucleic acids (DNAs), aggregates of the desired protein, endotoxins, viruses, protein A detached from the column, and aggregates of protein A and antibodies from the sterilized solution (a downstream step).

The concentration of a desired protein in a cell culture subjected to a conventional purification method for a protein as described above is now typically on the order of 1 g/L. The concentration of contaminants is also probably almost comparable to or less than the concentration of the desired protein. In such a concentration, even a conventional purification method for a protein comprising the harvest step and the downstream step can be useful.

However, because the demand for antibody drugs rapidly grows and the production of proteins used in the antibody drugs has been large-scale-oriented, cell culture technologies for increasing the concentration of proteins in cell cultures have been rapidly advanced in recent years. Thus, the concentration of desired proteins in cell cultures sometimes reaches 10 g/L or more. At the same time, the concentration of contaminants in the cell cultures similarly increases; it is becoming difficult to purify desired proteins by conventional purification methods for proteins.

Particularly, an increased concentration of a desired antibody protein in a cell culture also tends to noticeably increase the concentration of aggregates of its monomer, for example, multimers such as a dimer and a trimer. Such aggregates can cause complement activation or anaphylaxis when they are administered into a living body. It is therefore pointed out that the aggregates can deleteriously affect the safety of the antibody drug; an effective method for the removal thereof has been strongly desired in recent years. For solving the problem, chromatography processes are reported in large numbers which aim to effectively remove various contaminants including the aggregates to purify antibody proteins used as antibody drugs, namely a monoclonal antibody, a polyclonal antibody, a humanized antibody, a human antibody, an immunoglobulin, and the like.

Ion-exchange chromatography is a method for separating an antibody and contaminants by utilizing the difference of their isoelectric points. Particularly, anion-exchange chromatography is frequently used for removing contaminants such as HCP, DNA and virus generally having lower isoelectric points than antibody proteins. A method for purifying an antibody monomer by removing aggregates having isoelectric points almost equal to that of the monomer is also proposed.

For a method for removing common contaminants such as HCP, protein adsorption membranes to which protein adsorption capability is imparted by introducing ion-exchange groups into the porous membrane have recently been developed (see, for example, Patent Literatures 1 and 2). As a usage example of protein adsorption membranes, Patent Literature 3 also discloses a method for separating albumin from a lymph fluid using two types of protein adsorption membranes, i.e. a porous cellulose membrane into which anion-exchange groups are introduced and a porous cellulose membrane into which cation-exchange groups are introduced. Further, Patent Literature 4 discloses a method for separating nucleic acid and endotoxin using a porous cellulose membrane into which anion-exchange groups are introduced. Further, Patent Literatures 5 and 6 also disclose protein adsorption membranes in each of which cation-exchange groups and anion-exchange groups are introduced into a porous polyether sulfone membrane.

In addition, Patent Literature 7 discloses a porous membrane having a swollen gel layer in which a primary amine is immobilized as an anion-exchange group, as a porous membrane suitable for purifying an antibody monomer by removing impurities from a solution in a state of a relatively high salt concentration, that is, of high electric conductivity, such as a cell culture or an eluate of a cation-exchange chromatography step.

As a method for removing antibody aggregates, for example, Patent Literature 8 also discloses a purification method for an antibody monomer, which involves adjusting a mixed solution of the antibody monomer and aggregates to a pH near the isoelectric point of the antibody, passing the mixed solution through an anion-exchange chromatography column and recovering the passed solution, further passing buffer solutions of the same pH therethrough and recovering the wash solutions, and using these recovered solutions as purified solutions of the antibody monomer. This purification method is based on the principle that the aggregate is easily, although slightly, immobilized by anion-exchange groups compared to the monomer, because it has more charge points than the monomer. Patent Literature 9 also discloses a purification method for an antibody monomer, which involves adsorbing the antibody monomer and aggregates to an anion-exchange chromatography column and performing gradient elution in which the salt concentration in the eluate is gradually increased to collect the elution peak fraction of the antibody monomer first eluted.

It has been widely studied in recent years to use a chromatography column packed with mixed-mode resins having a plurality of ligands in order to efficiently separate and purify an antibody from contaminants. Ligands called mixed mode ligands or multi-modal ligands are used in such a chromatography. Chromatography using such ligands is expected to be capable of simultaneously and effectively removing a plurality of contaminants as well as enabling higher-precision separation by utilizing a plurality of differences in interactions: a difference in charge interaction and a difference in hydrophobic interaction.

For example, Patent Literature 10 describes a method which involves adsorbing contaminants and recovering an antibody monomer in a flow-through mode using chromatography with multi-modal ligands consisting of an anion-exchange group and a hydrophobic group, particularly a method which involves adsorbing and removing an aggregate consisting of a liberated protein A ligand and an antibody monomer. Patent Literature 11 also describes a method which involves adsorbing most contaminants such as DNA, virus, endotoxin, aggregates, and HCP using chromatography with multi-modal ligands having a quaternary ammonium group, a hydrogen-bonding group, and a hydrophobic group and recovering an antibody monomer by flow-through, and particularly describes that HCP is almost completely removed. In addition, Patent Literature 12 describes purifying an antibody monomer in a binding mode by using chromatography with mixed mode ligands having a mercapto group and an aromatic pyridine ring to adsorb only the antibody monomer and remove aggregates as non-adsorption fractions.

Patent Literature 13 describes an example in which chromatography with hydroxyapatite was applied as a method for purifying and recovering an antibody monomer in a flow-through mode intended for selectively adsorbing aggregates to a column and more effectively removing the aggregates. Patent Literature 7 also describes a porous membrane in which an anion-exchange group using an amino group is immobilized on the surface of a substrate via graft chains, and discloses a method for immobilizing limited amino groups by a gas phase reaction. In addition, Patent Literature 8 describes a method for separating an egg-white protein using a porous membrane on which diethylamino groups and 2-hydroxyethylamino groups are immobilized via graft chains.

CITATION LIST

Patent Literature
Patent Literature 1: U.S. Pat. No. 5,547,575
Patent Literature 2: U.S. Pat. No. 5,739,316
Patent Literature 3: U.S. Pat. No. 6,001,974
Patent Literature 4: U.S. Pat. No. 6,235,892
Patent Literature 5: U.S. Pat. No. 6,783,937
Patent Literature 6: U.S. Pat. No. 6,780,327
Patent Literature 7: Japanese Patent Laid-Open No. 2009-53191
Patent Literature 8: U.S. Pat. No. 6,177,548
Patent Literature 9: National Publication of International Patent Application No. 2002-517406
Patent Literature 10: National Publication of International Patent Application No. 2008-505851
Patent Literature 11: National Publication of International Patent Application No. 2008-517906
Patent Literature 12: National Publication of International Patent Application No. 2008-500972
Patent Literature 13: National Publication of International Patent Application No. 2007-532477
Patent Literature 14: Japanese Patent No. 2796995
Patent Literature 15: Japanese Patent Laid-Open No. 11-12300

SUMMARY OF INVENTION

Technical Problem

As described above, many methods are proposed and reported for separating an antibody with high precision from a wide variety of contaminants in a cell culture. However, it is even now difficult to purify an antibody by effectively and rapidly removing all contaminants; particularly, in an intermediate purified solution having a high salt concentration after an affinity chromatography, there is concern that it becomes further difficult under circumstances in which the concentration of a desired protein in a cell culture is being drastically improved to remove HCP, aggregates and the like remaining in minute amounts to levels required for pharmaceutical preparations to recover a high-precision antibody monomer. It is also extremely difficult to effectively perform the purification of an antibody monomer, particularly purification intended for the removal of aggregates.

The protein adsorption membranes disclosed in Patent Literatures 1 to 6 are poor in the ability to remove cell debris as turbid impurities, because they have pore diameters of 1 μm or more. The membranes cannot also adsorb a large amount of protein, because they have small capacities of adsorbing dissolved protein. In addition, although a salt is typically contained in a cell culture, a salt content of 0.1 mole/L or more in the cell culture markedly reduces the protein adsorption amount of the protein adsorption membranes disclosed in Patent Literatures 1 to 6. Thus, it is not practical to remove impurity proteins from a cell culture having high electric conductivity or an eluate of a cation-exchange chromatography step using any of the protein adsorption membranes disclosed in Patent Literatures 1 to 6.

The porous membrane disclosed in Patent Literature 7 exhibits noticeable protein adsorption for a solution containing salt and having high electric conductivity. However, because of its too high adsorption performance, it is difficult to selectively adsorb and remove only impurity proteins; a desired protein also tends to be adsorbed. This poses the problem that the recovery rate of the desired protein is reduced. The practical problem also arises that the membrane cannot be repetitively used, because the adsorbed impurities cannot be sufficiently washed and eluted.

The methods using anion-exchange chromatography columns disclosed in Patent Literatures 8 and 9 require the extremely strict control of conditions and a resolution capability, because they utilize only a slight difference in the charge interaction to remove aggregates. For that reason, it is difficult to pass liquid through the column at a high flow rate and the method is unsuitable for rapid treatment.

The multi-modal ligands disclosed in Patent Literatures 10 and 11 similarly use only the beads for the chromatography column as the subject of ligand immobilization, which makes it difficult to pass liquid through the column at a high flow rate. The mixed mode ligands disclosed in Patent Literatures 12 and 13 also use only the beads for the chromatography column as the subject of ligand immobilization, which makes it difficult to pass liquid through the column at a high flow rate. This is because the bead used for chromatography is a porous particle and proteins contact the ligands only and essentially by which a solution enters into the pore of the porous body through diffusion. Thus, for column chromatography using common beads, the liquid-passing rate for effective adsorption is on the order of 100 V/h (the passing of a solution in an amount of 100 times the column volume per hour).

Patent Literature 14 describes a porous membrane in which an anion-exchange group using an amino group is immobilized on the surface of a substrate via graft chains; however, it does not describe a method for purifying a protein by using the resultant porous membrane. Patent Literature 15 also describes a method for separating an egg-white protein by using a porous membrane in which diethylamino groups and 2-hydroxyethylamino groups are immobilized via graft chains; however, it limits the protein to the egg-white protein and does not describe a method for purifying an antibody monomer.

The difficulty of purifying an antibody by effectively and rapidly removing all contaminants is also attributed to the fact that it is not easy to determine effective conditions of pH, salt concentration, solution composition, and the like for effectively separating and purifying an antibody in both the flow-through mode and the binding mode, that is, to determine stable and versatile purification conditions, since conventional purification technologies have narrow process windows. This situation is also similar for the chromatography with mixed mode ligands intended for the more efficient removal of contaminants.

In addition, the step of removing contaminants in intermediate purification is oriented to a process using a chromatography column of high resolution, because high precision is required. Particularly for the removal of contaminants such as HCP as required to be made from in a state removed to a low concentration by affinity chromatography to in a more removed state, the setting of conditions becomes more difficult, all the more because they have narrow process windows. Further, aggregates, which have interaction properties close to those of an antibody monomer, find in difficulty particularly in the setting of conditions, having previously made the rapid removal thereof using an adsorption membrane or the like impossible. Thus, a method for removing contaminants from an antibody monomer by using a porous membrane has not previously been reported.

In view of such circumstances, an object of the present invention is to provide a method for purifying a protein by using a porous membrane capable of effectively and rapidly removing contaminants such as HCP, DNA, endotoxin, lipid, virus, and protein aggregates of a protein including a desired protein, with simplicity, rapidity and a wide process window, from a solution having high electric conductivity and containing proteins such as an antibody monomer and contaminants in high concentrations. Another object of the present invention is to provide a method for purifying a protein by using a porous membrane capable of being reused by washing adsorbed impurities by suitable washing after trapping contaminants.

Solution to Problem

As a result of intensive studies for solving the above-described problems, the inventors have found that the use of a porous membrane having a porous substrate, amino groups bonded to side chains of graft chains immobilized on the surface of the porous substrate and alkyl groups bonded to the alkyl groups is effective in removing contaminants having previously been difficult to remove, including aggregates including a dimer, thereby accomplishing the present invention.

Thus, an aspect of the present invention inheres in a method for purifying an antibody monomer, comprising: providing a porous membrane comprising a hydrophobic porous substrate, a hydrophilic molecular chain of a different material from that of the porous substrate, immobilized on the surface of pores of the porous substrate, and a side chain of the molecular chain, containing a nitrogen atom to which one to three alkyl groups each having two or three carbon atoms are bonded; passing an antibody solution containing antibody aggregates of dimers or higher-order multimers through the porous membrane to adsorb the antibody aggregates to the porous membrane; and recovering the purified antibody monomer in the passed solution.

Another aspect of the present invention inheres in a method for purifying an antibody monomer solution having a salt concentration of 0.3 mole/L or less, comprising a step of filtering the antibody monomer solution through a porous membrane to adsorb impurities contained at least in the antibody monomer solution to the porous membrane, and recovering the filtered antibody monomer solution, wherein the porous membrane comprises a hydrophobic porous substrate, a hydrophilic molecular chain of a different material from that of the porous substrate, immobilized on the surface containing pores of the porous substrate, and a side chain containing a nitrogen atom to which one to three alkyl groups are bonded, a hydroxyl group, and a carbonyl group.

Advantageous Effects of Invention

According to the method for purifying a protein by using a porous membrane according to the present invention, contaminants such as HCP, DNA, endotoxin, virus, and protein aggregates can be removed with simplicity and rapidity from a solution having a relatively high salt concentration, containing proteins such as an antibody and the contaminants, enabling the effective and rapid purification of a protein monomer such as an antibody.

DESCRIPTION OF EMBODIMENTS

Modes for carrying out the present invention (hereinafter referred to as "the present embodiments") will be described below in detail. In this respect, the present invention is not intended to be limited to the following present embodiments, and various modifications can be made within the scope of the gist of the invention.

The porous membrane according to the present embodiment comprises a hydrophobic porous substrate, a hydrophilic molecular chain of a different material from that of the porous substrate, immobilized on the surface containing pores of the porous substrate, and a side chain containing at least one amino group selected from a propylamino group, an isopropylamino group, a diethylamino group, a triethylamino group, and a tripropylamino group. The method for producing an antibody monomer according to the present embodiment comprises: providing a porous membrane according to the present embodiment; passing an antibody monomer solution containing impurities through the porous membrane to adsorb the impurities to the porous membrane; and recovering the purified antibody monomer in the solution at a recovery rate of 80% or more.

The "antibody" according to the present embodiment is a generic term applied to a protein causing an antigen-antibody reaction with antigen and adding immunity against the antigen to a living body, and specifically refers to a monoclonal antibody, a polyclonal antibody, a humanized antibody, a human antibody, an immunoglobulin, and the like.

Particularly, from a view point that the purification method according to the present embodiment can be used in a production step of an antibody drug, an antibody capable of being an antibody drug among the above antibodies is suitable as an object to be purified by the purification method according to the present embodiment. The "antibody monomer" according to the present embodiment refers to one present in the form of a monomer.

The "contaminant" according to the present embodiment refers to an impurity other than an antibody monomer, contained in a solution (mixed solution) from which the antibody monomer is to be purified. Examples thereof include impurities other than a desired antibody monomer, produced in a culture tank when the antibody is produced by cell culture. More specific examples of the "contaminant" include aggregates of the antibody monomer, species of the misfolded antibody protein, HCP, endotoxin, DNA, protease, liberated protein A, virus, and bacteria.

The "aggregate" (sometimes referred to as an "aggregate of an antibody monomer") according to the present embodiment refers to a complex of monomers of one or a plurality of antibodies, or a complex of an antibody monomer and a compound such as a different protein; examples thereof include a multimer such as a dimer or trimer of antibody monomers and a complex of liberated protein A and an antibody.

The "mixed solution containing an antibody monomer and contaminants" according to the present embodiment is not particularly limited, provided that it is a solution containing (or a solution potentially containing) the above described antibody monomer and contaminants, and is a solution from which the antibody monomer is to be purified by the method for purifying an antibody monomer according to the present embodiment. Examples thereof include a cell culture or its clarified solution used for the production of an antibody or a partially purified solution during or after a chromatography step in a downstream step therefor.

Among these, a clarified solution typically before an affinity chromatography step using protein A or a partially purified solution after an affinity chromatography step in the downstream step is suitable as an object to be purified for the purification method according to the present embodiment, since these solutions are clear and the partial removal of contaminants further reduces the load in a subsequent purification step. The concentrations of an antibody monomer and contaminants in the mixed solution are not particularly limited. However, in view of the fact that the method for purifying an antibody monomer according to the present embodiment can also be efficiently performed particularly on a mixed solution containing high concentrations of the antibody monomer and contaminants, the mixed solution may contain 2 g/L or more of the total of the antibody monomer and contaminants, for example. In addition, the mixed solution may contain 5 g/L or more of an antibody monomer, or may contain 1 g/L or more of contaminants.

The "porous membrane" used in the present embodiment has a hydrophobic porous substrate, a hydrophilic molecular chain of a different material from that of the porous substrate, immobilized on the surface containing pores of the porous substrate, and a side chain of the molecular chain, containing at least one amino group selected from a propylamino group, an isopropylamino group, a diethylamino group, a triethylamino group, and a tripropylamino group. In the following description, the hydrophilic molecular chain immobilized on a porous substrate is referred to as "graft chain". All the surface of a porous substrate including the side walls of pores in the interior of the porous substrate is simply referred to as "surface", and the surface not including the side walls of pores in the interior of the porous substrate is referred to as "main surface".

The porous membrane used in the present embodiment utilizes the fact that the combination of an amino group and an alkyl group produces differences in the adsorption performance and purification conditions depending on the protein. Thus, it is possible to obtain a porous membrane for protein purification, having a wide process window, by selecting the combination of an amino group and an alkyl group according to the purpose. Particularly when an antibody protein is intended to be purified, a propylamino group ($—N—CH_2CH_2CH_3$) and an isopropylamino group ($—N—CH(CH_3)_2$) are preferable as secondary amino groups. A diethylamino group ($—N—(CH_2CH_3)_2$) and a diisopropylamino group ($—N—(CH(CH_3)_2)_2$) are preferable as tertiary amino groups. A triethylamino group ($—N^+—(CH_2CH_3)_3$), a tripropylamino group ($—N^+—(CH_2CH_2CH_3)_3$), and a tridipropylamino group ($—N^+—(CH(CH_3)_2)_3$) are preferable as quaternary amino groups. It should be noted that the secondary amino group, the tertiary amino group, and the quaternary amino group are also called a monoalkyl-substituted amino group, a dialkyl-substituted amino group, and a trialkyl-substituted amino group, respectively.

An amine having the larger number of carbon-containing groups and a higher hydrophobicity is generally predicted to increase the protein-adsorbing capability thereof at a high salt concentration. This is because an amine having the larger number of carbon-containing groups strengthens the electrostatic interaction between the carboxylic acid of protein and the amine, and the higher hydrophobicity thereof more easily causes adsorption due to hydrophobic interaction. However, the larger number of carbon-containing groups of the amine tends to increase the attenuation of the electrostatic interaction when the salt concentration is increased. The higher salt concentration also tends to strengthen the hydrophobic interaction. Thus, it is difficult to theoretically predict a functional group having adsorption property even at a high salt concentration, based on only the number of carbon-containing groups of an amine and the type of an alkyl group. In the present embodiment, the effective combination of electrostatic interaction and hydrophobic interaction has been determined from the results obtained by experimental evaluation.

As a result, among the above-described combinations of amino groups and alkyl groups, a propylamino group, an isopropylamino group, a diethylamino group, a triethylamino group, and a tripropylamino group have been found to be more preferable in order to achieve adsorption at a high salt concentration.

In addition, since a hydroxyl group and a carbonyl group are preferably contained in the side chain, hydrophilicity, a hydrogen-bonding property, and a moderate cation exchange property are synergized in addition to the anion exchange property due to an amino group and the hydrophobicity due to an alkyl group, thereby enabling the purification of a protein with a wider process window.

The raw material of the porous substrate is not particularly limited; however, it is preferably composed of a polyolefin polymer in view of the fact that if it is hydrophobic, an additional hydrophobic interaction can occur between the protein and the porous substrate and in view of retaining mechanical properties. Examples of the polyolefin polymer include a homopolymer of an olefin such as ethylene, propylene, butylene, and vinylidene fluoride, a copolymer of two or more of the olefins, or a copolymer of at least one of the olefins and a perhalogenated olefin. It may be a mixture of two or more of these polymers. Examples of the perhalogenated olefin include tetrafluoroethylene and chlorotrifluoroethylene.

Among these, polyethylene or polyvinylidene fluoride is preferable and polyethylene is more preferable as a raw material of the porous substrate in view of the fact that they are excellent particularly in hydrophobicity and mechanical strength and provides high adsorption capacity.

A method for immobilizing an alkylated amino group on the porous substrate is not particularly limited; however, it can typically be carried out by a method which involves introducing a highly reactive functional group, such as an epoxy group, onto the surface of the porous substrate and then bonding an organic amine compound to the functional group. According to the present embodiment, graft chains having epoxy groups are immobilized on the surface of the porous substrate in advance, followed by reacting the epoxy group with an organic amine compound composed of a desired combination of an amino group and an alkyl group to immobilize the organic amine compound on the main surface of the porous substrate and the side walls of the pores provided in the porous substrate.

The "graft chain" according to the present embodiment is a molecular chain formed of a different material from that of the porous substrate, bonded to the main surface of the porous substrate and the side walls of the pores provided in the porous substrate, and can be present in both the interior of the substrate backbone forming the substrate and the interior of the pores forming the porous parts. Examples of the graft chain include molecular chains comprising glycidyl methacrylate, glycidyl acrylate, glycidyl sorbate, glycidyl itacolate, glycidyl maleate, vinyl acetate, hydroxypropyl acetate, or a polymer of two or more of these monomers. Among others, a polymer of glycidyl methacrylate is preferable, because the ring-opening of the epoxy group facilitates the introduction of an amino group, and a hydroxyl group and a carbonyl group can be easily introduced into the side chain. The binding rate of the graft chains to the porous substrate (graft rate) can be measured by using a technique as described, for example, in Examples and the like to be described later, and is preferably 10% to 200%, more preferably 20% to 150%, still more preferably 30% to 100% in view of securing both higher adsorption capacity and mechanically stable strength.

The amino groups are preferably introduced into 60% to 97% (both inclusive), more preferably 70% to 96% (both inclusive), of all of the side chains of the graft chains. The epoxy group into which amino group has not been introduced is preferably ring-opened and diolized by alkali solution treatment or the like to inhibit it from chemically binding to proteins. That which the side chains have diol groups may increase the hydrophilicity of the graft chains. Thus the graft chains may be effectively dispersed in pores filled with a solution. The side chains of the graft chains having diol groups are preferably 3% to 40% (both inclusive), more preferably 4% to 30% (both inclusive), of all of the side chains. A percentage of diol groups of more than 40% tends to reduce the effect of anion-exchange interaction due to amino groups.

As a method for introducing graft chains onto the surface of the porous substrate and the side walls of the pores thereof and further immobilizing alkylated amino groups on the graft chains, a method disclosed in Japanese Patent Laid-Open No. 02-132132 can be exampled without being limited thereto. Since this method follows a gas phase reaction, the amine compound is limited to one which is present as a gas phase in a reaction environment and can react with an epoxy group. As a method for immobilizing an amine compound by reaction with an epoxy group immobilized on the graft chain in a liquid phase reaction, a method described in Journal of Chromatography A, 689 (1995) 211-218 can be exampled. However, the literature discloses only a method which involves reacting diethylamine. The method for reacting any amine compound with an epoxy group for immobilization needs to be properly selected depending on the amine compound used; for example, a method as described in Examples and the like to be described later is used.

The porous membrane used in the present embodiment comprises a porous substrate, a graft chain immobilized on the main surface of the porous substrate and the side walls of the pores provided in the porous substrate, and an amino group and an alkyl group bonded to the side chain of the graft chain. Such a porous membrane has a structure in which each graft chain immobilized on a porous substrate has at least one side chain and at least one each of an amino group and an alkyl group are immobilized on the side chain. Thus, the amino and alkyl group is three-dimensionally distributed in a pore space. Hence, the number of absorption points of amino groups to a protein and the like having charge points is large; as the adsorption amount is increased, the capability of adsorbing a protein exhibiting weak interaction is also increased. In addition, besides the charge interaction due to anion exchange, the porous membrane has the effect of achieving more highly selective protein adsorption by the presence of an alkyl group, a hydroxyl group and a carbonyl group. Particularly, it is possible to effectively separate and purify a protein such as an antibody that is difficult to be purified only by charge interaction from contaminants. The porous membrane is suitable particularly for the purpose of rapidly and efficiently performing antibody purification by passing a solution containing an antibody monomer and contaminants therethrough to selectively adsorb only the contaminants as well as passing the antibody therethrough without adsorption.

The maximum pore diameter of the porous membrane is preferably 0.01 μm to 5.0 μm, more preferably 0.1 μm to 3.0 μm, still more preferably 0.1 μm to 1.0 μm in a state before the immobilization of anion-exchange groups and the introduction of graft chains, in view of effectively adsorbing an antibody monomer and/or contaminants in a solution and obtaining a high flux.

The porosity, which is the percentage of the volume of pores in the total volume of the porous membrane, is not particularly limited, provided that it retains the shape of the porous membrane and the amount of pressure loss in liquid-passing is at a practically problem-free level; however, it is preferably 5% to 99%, more preferably 10% to 95%, still more preferably 30% to 90%.

The pore diameter and the porosity can be measured by a method known to those of ordinary skill in the art as described in Marcel Mulder, "Membrane Technology" (published by IPC) or the like. Examples thereof include measurement methods such as observation under an electron microscope, a bubble point method, a mercury press-in method, and a transmittance method. For example, the maximum pore diameter can be measured by properly using the bubble point method described in Examples and the like to be described later.

The form of the porous substrate is not particularly limited, provided that it is a form enabling the passing of a solution therethrough; examples thereof include a flat membrane, a nonwoven fabric, a hollow fiber membrane, a monolith, or a capillary. Among these forms, the hollow fiber membrane is preferable in view of ease of production, scale-up properties, membrane packing properties in modular molding, and the like. The shape of the porous substrate may be, for example, disc-shaped or cylinder-shaped, but is not limited thereto.

The hollow fiber membrane according to the present embodiment is a cylinder-shaped or fiber-shaped porous membrane having hollow parts, and means a porous body having properties in which the internal layer and external layer of a hollow fiber communicate with each other through pores as through-holes and a liquid or a gas is passed therethrough via the pores from the internal layer to the external layer or from the external layer to the internal layer. The outer diameter and inner diameter of the hollow fiber are not particularly limited, provided that the porous membrane can physically retain its shape and can be subjected to module molding.

The step of passing a mixed solution containing an antibody monomer and contaminants through the above-described porous membrane according to the present embodiment to adsorb the contaminants and/or the antibody monomer to the porous membrane will be described below.

Examples of a typical method for purifying an antibody monomer according to the present embodiment are not particularly limited; however, a method which involves passing a mixed solution containing the antibody monomer and contaminants through the porous membrane according to the present embodiment, adsorbing the contaminants in the mixed solution to the porous membrane to remove the contaminants from the mixed solution, and recovering the passed solution as a purified solution of the antibody monomer is preferable, since it is most simple and enables purification to be rapidly performed.

The isoelectric point (pI) of an antibody monomer is typically in the range of 6.5 to 8.5. On the other hand, the pIs of most contaminants such as HCP, DNA and virus are 6 or less. Thus, most contaminants can be adsorbed to positively charged amino groups on the porous membrane by suitably controlling the pH range and salt concentration (electric conductivity) of a solution passed through the porous membrane to recover the passed solution as a purified solution of the antibody monomer. Among contaminants, an aggregate has a pI close to or nearly equal to that of the antibody monomer. However, the antibody monomer and the aggregate differ in that because the aggregate is a complex of the antibody monomers, although it has a pI comparable to that of the antibody monomer, the aggregate has more charge points per molecule. Thus, the aggregate has a property of being slightly more easily adsorbable to the porous membrane having positively charged amino groups than the antibody monomer. For that reason, the suitable adjustment of the pH and salt concentration of the solution enables the adsorption of the aggregate to amino groups on the porous membrane and the recovering of the passed solution as a purified solution of the antibody monomer.

Particularly when a porous membrane having amino groups immobilized on a porous substrate via graft chains (preferably, a porous membrane in which each graft chain has at least one side chain and each side chain has an amino group) is used, the amino groups will be three-dimensionally immobilized on the porous membrane. As a result, proteins such as aggregates are three-dimensionally immobilized by a plurality of amino groups at charge points. For that reason, the aggregates tend to be more firmly adsorbed to the porous membrane than the antibody monomer, enabling the purification of the antibody monomer to be easily performed.

Protein, DNA, virus, and the like essentially also have properties other than anion exchange interaction, such as hydrophobic interaction. For that reason, an antibody can be more easily purified by using a porous membrane having properties in which hydrophobicity, a hydrogen-bonding property, and a cation exchange property are properly controlled. Thus, the graft chain can have suitable alkyl groups, hydroxyl groups and carbonyl groups to more selectively adsorb and remove contaminants. Particularly, an aggregate of an antibody monomer differs in hydrophobic properties from the antibody monomer. Thus, the graft chain can have an alkyl group to more selectively adsorb and remove the aggregate.

When contaminants in the mixed solution are adsorbed to a porous membrane to remove the contaminants from the mixed solution by adsorption to recover the passed solution as a purified solution of an antibody monomer, the pH and salt concentration of the mixed solution are adjusted to conditions under which the adsorption of the contaminants (particularly, aggregates) to the porous membrane becomes more noticeable than that of the antibody monomer. Specifically, the mixed solution is preferably adjusted to a pH of 6 to 9 and a salt concentration of 0 mole/L to 0.3 mole/L (both inclusive).

Examples of the salt used for the adjustment of the salt concentration include, but not limited to, a metal salt of citric acid, phosphoric acid or glycine in addition to sodium chloride, sodium sulfate, sodium acetate, ammonium sulfate, and the like. The pH adjustment can typically be conveniently performed by adding hydrochloric acid or sodium hydroxide; however, it is not limited thereto and can be carried out properly using a method for adjusting pH that is known to those of ordinary skill in the art. The pH and salt concentration of the solution can be measured by a method that is known to those of ordinary skill in the art by using, for example, a commercial measuring apparatus.

The mixed solution having the above pH and salt concentration is passed through the porous membrane according to the present embodiment to adsorb contaminants having a pI of 6 or less such as aggregates, HCP, DNA, endotoxin, and virus to the porous membrane. The contaminants (particularly, aggregates) are more selectively adsorbed to the porous membrane by adjusting the pH and salt concentration of the mixed solution depending on the pI of an antibody monomer to be purified, enabling the purification of the antibody monomer to be effectively performed. In view of the fact that the pI of a common antibody monomer is near 8, the acidity of the mixed solution is preferably pH 6 to 9, more preferably pH 7 to 8.5, still more preferably pH 7.5 to 8.5. The salt concentration of the mixed solution is preferably 0 mole/L or more, more preferably 0.01 mole/L or more, still more preferably 0.02 mole/L or more. Preferred is also 0.3 mole/L or less, more preferably 0.2 mole/L or less, still more preferably 0.1 mole/L or less, most preferably 0.05 mole/L or less.

Specifically, depending on the antibody monomer to be purified, the pH and salt concentration of the mixed solution can be set to the above range to effectively perform the purification of the antibody monomer when the isoelectric point of the antibody monomer is in the range of 7.5 or more, for example, 7.5 to 8.5. The porous membrane after passing the mixed solution can be washed with a wash solution having the same pH and salt concentration as those of the mixed solution to purify the antibody monomer in higher yield.

Thus, the mixed solution containing the antibody monomer and contaminants can be adjusted for pH and the salt concentration and passed through the porous membrane according to the present embodiment to easily remove the contaminants including aggregates to simply perform the purification of the antibody monomer. Here, because the contact between the passed solution and amino groups and alkyl groups immobilized on the porous membrane is made by forced convection, the antibody monomer can be purified even at a very fast liquid-passing rate compared to the case of column chromatography, for example, at a flow rate of 1,000 V/h or more.

By using the method and porous membrane according to the present embodiment and referring to the description of the present specification, contaminants can be simply removed with rapidity and a wide process window from a solution containing a high concentration of an antibody and a high concentration of contaminants and further containing a salt. This enables the antibody to be effectively and rapidly purified from the solution. Thus, a purified antibody can be industrially and efficiently obtained.

The present embodiment is more specifically described below based on Examples and Comparative Examples (hereinafter, sometimes simply referred to as "Examples and the like"). However, the scope of the present embodiment is not intended to be limited to only the following Examples.

Production Example 1

Preparation of Porous Membrane Module Having Anion Exchange Group Immobilized on Surface Thereof (i) Introduction of Graft Chain into Hollow Fiber-Shaped Porous Substrate Polyethylene-made hollow fiber-shaped porous substrates (Polyethylene B membrane from Asahi Kasei Chemicals) having an outer diameter of 3.1 mm, an inner diameter of 2.1 mm, a length of 100 mm, a porosity of 70%, a weight of 0.135 g and a maximum pore diameter of 0.3 μm measured by the bubble point method to be described later was placed in an airtight container, and the air in the container was replaced with nitrogen. Then, the materials were irradiated with 200 kGy of γ-ray while cooling the container from the outside thereof with dry ice to generate radical. The resultant radical-containing polyethylene-made hollow fiber-shaped porous substrates were placed in a glass reaction tube, and the oxygen in the reaction tube was removed by depressurizing to 200 Pa or less. A reaction solution consisting of 2.5 parts by volume of glycidyl methacrylate (GMA) and 97.5 parts by volume of methanol, adjusted at 40° C., was injected into 20 parts by mass of the hollow fiber-shaped porous substrates, which was then allowed to stand in a closed state for 12 hours for graft polymerization reaction to provide hollow fiber porous membranes having graft chains introduced. In this respect, the reaction solution consisting of GMA and methanol was bubbled with nitrogen to replace the oxygen in the reaction solution with nitrogen in advance.

After graft polymerization reaction, the reaction solution in the reaction tube was discarded. The hollow fiber porous membranes were then washed by placing dimethylsulfoxide in the reaction tube to remove the residual glycidyl methacrylate, its oligomers and graft chains that were not immobilized on the hollow fiber porous membranes. After discarding the wash solution, washing was further carried out twice by placing dimethylsulfoxide therein. After discarding the wash solution, washing was further carried out twice by placing dimethylsulfoxide therein. Then, washing was similarly carried out using methanol for three times. When the hollow fiber porous membranes after washing were dried and weighed, the weight of the hollow fiber porous membranes was 155% (0.209 g) of that before introduction of graft chains. The graft rate defined as the ratio of the graft chain weight to the porous substrate weight before the graft chain introduction was 55%. The hollow fiber after reaction had an outer diameter of 3.35 mm, an inner diameter of 2.15 mm, and a length of 108 mm.

(ii) Immobilization of Amino Group and Alkyl Group on Graft Chain

The hollow fiber porous membranes dried after graft chain introduction were swollen by immersion in methanol for 10 minutes or more, and then subjected to water replacement by immersion in pure water. Then, as amine compounds having an amino group and an alkyl group were provided isopropylamine, normal propylamine, butylamine, dimethylamine, diethylamine, dipropylamine, trimethylamine, triethylamine, and tripropylamine. In addition, the epoxy groups which the graft chains have were replaced with an amine compound by a ring-opening reaction under reaction conditions suitable for each amine compound as described in Examples and Comparative Examples to be described later to immobilize amino groups and alkyl groups on the graft chains. The replacement ratio T was expressed by the following equation (1):

$$T = N_1/N_0 \quad (1)$$

where $N_1$ is the number of moles of the epoxy groups replaced by the amine compound among the number ($N_0$) of moles of the epoxy groups.

When $N_1=N_0$, $T=1$, showing a state in which 100% of the epoxy groups are replaced with the amine compound. When $T=1$, no diol group is present on the graft chains.

Epoxy groups not replaced by an amine compound will be converted to diol groups by reaction with water under strongly alkaline reaction conditions. Hence, T is analytically obtained by solving a linear equation expressed by the following equation (2):

$$1 = \{(W_2 - W_1)/(M_1 T + M_0(1-T))\}/\{W_1(dg/(dg+100))/M_2\} \quad (2)$$

In the equation (2), $M_1$ is the molecular weight of an amine compound; $M_0$ is the molecular weight of water (18); $W_1$ is the weight of a hollow fiber porous membrane after the graft polymerization reaction; $W_2$ is the weight of a hollow fiber porous membrane after the amino group displacement reaction; dg is the graft rate; and $M_2$ is the molecular weight of GMA (142).

(iii) Preparation of Hollow Fiber Porous Membrane Module Having Amino Group and Alkyl Group Immobilized Both longitudinal ends of one hollow fiber porous membrane having amino groups and alkyl groups immobilized via graft chains, obtained in (ii), were fixed to a polysulfonate-made module case having an inner diameter of 0.5 cm and an effective length of 9.2 cm by using an epoxy potting agent so that the hollow parts of the hollow fiber porous membrane were not blocked to prepare a hollow fiber porous membrane module. This was used as an evaluation module in the following Examples and the like.

Evaluation Method Example 1

Bubble Point Method

The maximum pore diameter of the hollow fiber porous membrane was measured by using a bubble point method. One end of a hollow fiber porous membrane having a length of 8 cm was blocked, and the other end was connected to a nitrogen gas supply line via a pressure indicator. Nitrogen gas was supplied in this state to replace the inside of the line with nitrogen, followed by immersing the hollow fiber porous membrane in ethanol. At this time, the hollow fiber porous membrane was immersed in ethanol in a state only slightly pressurized with nitrogen to avoid backflow of ethanol into the line. The pressure of nitrogen gas was slowly increased in a state in which the hollow fiber porous membrane was immersed, and the pressure (P) at which bubbles of nitrogen gas started to stably occur from the porous fiber porous membrane was recorded. Using this, the maximum pore diameter of the hollow fiber porous membrane was calculated according to the following equation (3):

$$d = C_1 \gamma / P \quad (3)$$

where d is the maximum pore diameter and γ is surface tension. In the equation (3), $C_1$ is a constant. When ethanol is used as an immersion fluid, $C_1\gamma = 0.632$ (kg/cm); the maximum pore diameter d (μm) was determined by substituting P (kg/cm2) into the above equation.

Evaluation Method Example 2

Measurement of Protein Dynamic Adsorption Volume of Hollow Fiber Porous Membrane A bovine serum albumin (BSA) (from Sigma-Aldrich) solution in which BSA was dissolved at a concentration of 1 g/L in a 20 mmole/L Tris-HCl (pH 8.0) buffer containing 0 mole/L or 0.1 mole/L of sodium chloride was used to pass the BSA solution through the hollow fiber porous membrane module prepared in (iii) until the start of its breakthrough. In this respect, before passing the BSA solution therethrough, 20 mL of a 20 mmole/L Tris-HCl (pH 8.0) buffer was passed in advance to equilibrate the porous membrane. Here, the BSA solution containing 0 mole/L of sodium chloride had an electric conductivity of 1.3 mS/cm. The BSA solution containing 0.1 mole/L of sodium chloride had an electric conductivity of 10.2 mS/cm. The solution was passed at a flow rate of 3 mL/min from the inside of the hollow fiber porous membrane toward the outside thereof in the evaluation module. The evaluation was performed using AKTA-explorer100 from GE Healthcare Bioscience Corporation. Specifically, the time point at which the UV absorbance at 280 nm of the passed solution obtained using the apparatus reached 1/10 (15 mAU) of the UV absorbance (150 mAU) at 280 nm of the feed solution was defined as a breakthrough point, and the dynamic adsorption volume was calculated from the volume of the BSA solution that was fed until the time point. Here, from the concentration (Q) of a BSA solution, the volume ($V_B$) of the BSA solution passed through until the time the breakthrough of the evaluation module occurred, and the volume ($V_M$) of a hollow fiber porous membrane according to each Example in the evaluation module, the dynamic adsorption volume was calculated based on the following equation (4):

$$A = Q \times V_B / V_M \quad (4)$$

The volume of a hollow fiber porous membrane is the volume of the membrane from which the hollow parts are removed. The breakthrough refers to a time point at which the concentration of BSA in the passed solution has exceeded 10% (0.1 g/L) of the concentration of the BSA solution fed.

Evaluation Method Example 3

Evaluation of Selective Removal of Antibody Aggregate (i) Preparation of Antibody Protein Solution Containing Aggregate An antibody protein (Kenketsu Venoglobulin-IH from Benesis Corporation) was added to a 20 mmole/L Tris-HCl (pH 8.0) buffer containing 0 mole/L or 0.1 mole/L of sodium chloride to prepare a solution in which 1 mg/mL of the antibody protein was dissolved. Using the solution thus obtained as a feed solution, the feed solution equivalent to 100 volume based on the volume of the membrane contained in the hollow fiber porous membrane module was passed through the hollow fiber porous membrane module having any of various ligands prepared by the method of Production Example to measure the rate of recovery of the antibody protein after passage and the ratio of the antibody protein and a dimer that is the antibody aggregate.

(ii) Evaluation of Antibody Recovery Rate

The recovery rate of the antibody protein in the solution passed through the hollow fiber porous membrane module was evaluated by affinity chromatography. A high-performance liquid chromatography, LC-20A System from Shimadzu Corporation, was fitted with POROS G from Applied Biosystems (protein G column); a buffer (pH 7.0) in which 0.15 mole/L NaCl is contained in 50 mmole/L phosphoric acid was used to pass through the column at a flow rate of 2 mL/min and room temperature; and 100 μL of a sample was added thereto. A buffer in which 0.15 mole/L NaCl is contained in 12 mmole/L hydrochloric acid was used for elution. The antibody protein solution having a concentration of 1 mg/mL prepared in (i) was added as the sample, adsorbed to the protein G column, and further eluted from the protein G column; here, the peak area corresponded to the antibody protein concentration of 1 mg/mL. In addition, the solution passed through the hollow fiber porous membrane module was passed through the column in like manner for the determination of the elution peak area; the concentration of the antibody protein in the solution passed through the hollow fiber porous membrane module was calculated from the ratio of the above area and the elution peak area obtained from the 1 mg/mL antibody protein solution to provide the recovery rate.

(iii) Measurement of Ratio of Antibody Monomer and Antibody Aggregate

The ratio of the antibody monomer and the aggregate contained in the antibody protein was evaluated by gel filtration chromatography. A chromatograph, LC-20A System from Shimadzu Corporation, was fitted with TSKgel G3000SWXL from Tosoh Corporation as a gel filtration column; a buffer containing 0.1 mole/L phosphoric acid and 0.2 mole/L arginine (pH 6.8) was used to pass through the column at a flow rate of 0.8 ml/min and 25° C.; and 20 of an evaluation sample was added thereto. After passage through the column, the antibody monomer and the aggregate showed separated elution peaks; from the peak area ratio of the antibody monomer and aggregate obtained, the respective abundance percentages thereof in the solution were calculated. The percentages of dimers contained in the antibody protein before mixing used for evaluation and the antibody protein in the solution prepared in (i) were both 4.06%.

Evaluation Method Example 4

Impurity-Removing Capability and Recovery Rate of Antibody (i) Preparation of Solution Containing Impurity A cell culture obtained using CD OptiCHO (trademark) serum-free medium from Invitrogen was filtered and clarified using a microfiltration membrane having a maximum pore diameter of 0.45 μm (from Asahi Kasei Medical) to provide a clear cell culture. The resultant clear solution was desalted and concentrated using AKTAclossflow from GE Healthcare Bioscience Corporation to provide an impurities-concentrated solution of a cell culture containing HCP as the main ingredient. The protein concentration of the resultant impurity solution was 3 mg/mL when measured by Bradford method using bovine serum albumin as a standard protein (Bradford ULTRA kit from Novexin).

Then, an antibody protein (Kenketsu Venoglobulin-IH from Benesis Corporation) was provided. In addition, 0.1 mg/mL of impurities and 10 mg/mL of the antibody protein provided were dissolved in a 20 mmole/L Tris-HCl (pH 7.5) buffer containing 0.15 mole/L NaCl to provide a solution. Using the solution thus obtained as a feed solution, the feed solution was passed through the hollow fiber porous membrane module having any of various ligands prepared by the method of Production Example to measure the rate of recovery of the antibody protein and the concentration of the impurities after passage.

(ii) Evaluation of Antibody Recovery Rate and Impurity-Removing Capability

The recovery rate of the antibody protein in the solution passed through the hollow fiber porous membrane module and the concentration of impurity proteins consisting mainly of HCP were evaluated by affinity chromatography. A high-performance liquid chromatography, LC-20A System from Shimadzu Corporation, was fitted with POROS G from Applied Biosystems (protein G column) as an affinity column; a buffer (pH 7.0) in which 0.15 mole/L NaCl is contained in 50 mmole/L phosphoric acid was used to pass through the column at a flow rate of 2 mL/min and room temperature; and 100 μL of a sample was added thereto. A buffer in which 0.15 mole/L NaCl is contained in 12 mmole/L hydrochloric acid was used for elution. Thereafter, the elution peak of the antibody protein adsorbed to and eluted from the protein G column and the elution peak of the impurities having outflowed without adsorption to the column were displayed by the system. In addition, the recovery rate of the antibody in the solution and the impurity concentration were calculated from the elution peak area of the antibody protein and the elution peak area of the impurities.

The HCP concentration in the passed solution was quantitatively determined by an ELISA method using CHO Host Cell Protein ELISA Kit, 3rd Generation from CYGNUS. DNA contained in a trace amount was quantitatively determined on a fluorometer using dsDNA HS Assay Qubit Starter Kit from Invitrogen. The HCP concentration in the feed solution determined by the ELISA method was 87 μg/mL and the DNA concentration in this solution determined by the fluorometer method was 1.7 μg/mL.

(iii) Measurement of Ratio of Antibody Monomer and Aggregate in Solution Passed through Hollow Fiber Porous Membrane Module Because the antibody protein solution obtained as the solution passed through the hollow fiber porous membrane module contained impurities, only the antibody protein was isolated by affinity column chromatography, and the ratio of the antibody monomer and its aggregates was then determined by the method described in (ii) of Evaluation Method Example 3. HiTrap Protein G HP 1 ml from GE Healthcare Bioscience Corporation as an affinity column was attached to AKTAexplorer 100 from GE Healthcare Bioscience Corporation and equilibrated using a 20 mmole/L phosphate buffer (pH 7.0), and 2 ml of the solution was passed through the hollow fiber porous membrane module to adsorb only the antibody protein to the column. Subsequently, the column was washed with 10 ml of the equilibrating buffer, followed by eluting the adsorbed antibody protein using a 50 mmole/L citrate buffer (pH 3.3) to recover 3 ml of the isolated antibody protein solution; 17 ml of a 50 mmole/L Tris-HCl (pH 8.2) buffer solution was added thereto immediately for neutralization. The resultant isolated antibody protein solution was evaluated by the method of (ii) of Evaluation Method Example 3 to determine the ratio of the antibody monomer and the aggregates.

Example 1

Immobilization of Isopropylamino Group (Secondary Amino Group and Isopropyl Group) on Graft Chain The hollow fiber porous membrane having graft chains introduced obtained in (i) of Production Example 1 was swollen by immersion in methanol for 10 minutes or more, and subjected to water replacement by immersion in pure water. Isopropylamine was added to 20 mL of purified water while stirring to a total volume of 40 mL to prepare a reaction solution. In a glass reaction tube was then placed 25 parts by mass of the reaction solution based on the dry weight of the hollow fiber porous membrane having graft chains introduced obtained in (i) above, which was adjusted at 40° C. Thereafter, the hollow fiber porous membrane having graft chains introduced, after immersion in pure water was inserted into the reaction solution and allowed to stand for 48 hours to replace epoxy groups on the graft chains with isopropylamino groups to provide a hollow fiber porous membrane having secondary amino groups and isopropyl groups immobilized via the graft chains. The resultant hollow fiber porous membrane had an outer diameter of 3.43 mm and an inner diameter of 2.10 mm; from the equation (2), 72% of all of the epoxy groups which the graft chains had were found to be replaced by isopropylamino groups.

Using the hollow fiber porous membrane having isopropylamino groups, a hollow fiber porous membrane module was then prepared according to (iii) of Production Example 1. The volume of only the hollow fiber porous membrane in the hollow fiber porous membrane module, in which the hollow parts of the membrane are removed was 0.53 mL. The inner surface area of the hollow fiber porous membrane was 6.1 cm$^2$. When the BSA dynamic adsorption volume was determined according to Evaluation Method Example 2 using the resultant hollow fiber porous membrane module, it was 63 mg/mL for the sodium chloride concentration of 0 mole/L and 33 mg/mL for the sodium chloride concentration of 0.1 mole/L.

In addition, 20 mL of a 20 mmole Tris-HCl (pH 8.0) solution containing 1 mole/L NaCl (electric conductivity: 84 mS/cm) having an electric conductivity of 40 mS or more was passed through the hollow fiber porous membrane module after evaluating the BSA dynamic adsorption volume for the sodium chloride concentration of 0 mole/L to elute the adsorbed BSA. Thereafter, when the BSA dynamic adsorption volume of the hollow fiber porous membrane module for the sodium chloride concentration of 0 mole/L was again determined according to Evaluation Method Example 2, the same value of 63 mg/mL was obtained. Thus, the hollow fiber porous membrane module according to Example 1 could be properly washed and regenerated with a solution containing a high concentration of a salt.

The recovery rate and the dimer ratio after passing an antibody protein solution were also evaluated according to Evaluation Method Example 2. The recovery rate of the antibody was 89% for the sodium chloride concentration of 0 mole/L and 95% for the sodium chloride concentration of 0.1 mole/L. The dimer ratio was 1.03% for the sodium chloride concentration of 0 mole/L and 1.21% for the sodium chloride concentration of 0.1 mole/L. These results are shown in Table 1.

then prepared according to (iii) of Production Example 1. The volume of only the hollow fiber porous membrane in the hollow fiber porous membrane module, in which the hollow parts of the membrane are removed was 0.53 mL. The inner surface area of the hollow fiber porous membrane was 6.2 cm$^2$. When the BSA dynamic adsorption volume was determined according to Evaluation Method Example 2 using the resultant hollow fiber porous membrane module, it was 15 mg/mL for the sodium chloride concentration of 0 mole/L and 6 mg/mL for the sodium chloride concentration of 0.1 mole/L, showing decreased dynamic adsorption volumes.

In addition, 20 mL of a 20 mmole Tris-HCl (pH 8.0) solution containing 1 mole/L NaCl was passed through the hollow fiber porous membrane module after evaluating the adsorption of BSA for 0 mole/L to elute the adsorbed BSA. Thereafter, when the BSA dynamic adsorption volume of the hollow fiber porous membrane module for the sodium

TABLE 1

| | Amine Compound | Replacement Ratio [%] | BSA Dynamic Adsorption Volume [mg/mL] | | After Washing 0M NaCl | 0M NaCl Antibody Solution: Passage Amount 100 Membrane Volume | | 0.1M NaCl Antibody Solution: Passage Amount 100 Membrane Volume | |
|---|---|---|---|---|---|---|---|---|---|
| | | | 0M NaCl | 0.1M NaCl | | Antibody Recovery Rate [%] | Dimer Ratio [%] | Antibody Recovery Rate [%] | Dimer Ratio [%] |
| Example 1 | Isopropylamine (IPA) | 72 | 63 | 33 | 63 | 89 | 1.03 | 95 | 1.21 |
| Comparative Example 1 | Butylamine (BA) | 79 | 15 | 6 | 9 | 92 | 3.02 | 97 | 3.32 |
| Example 2 | Propylamine (PA) | 78 | 49 | 21 | 47 | 90 | 1.08 | 95 | 1.24 |
| Example 3 | Diethylamine (DEA) | 89 | 59 | 24 | 58 | 91 | 0.83 | 96 | 0.91 |
| Comparative Example 2 | Dimethylamine (DMA) | 69 | 22 | 11 | 21 | 93 | 3.13 | 97 | 3.65 |
| Comparative Example 3 | Dipropylamine (DPA) | 68 | 16 | 7 | 10 | 94 | 3.21 | 98 | 3.54 |
| Example 4 | Triethylamine (TEA) | 69 | 67 | 31 | 65 | 92 | 0.71 | 97 | 0.78 |
| Example 5 | Tripropylamine (TPA) | 63 | 53 | 28 | 50 | 89 | 1.05 | 96 | 1.23 |
| Comparative Example 4 | Trimethylamine (TMA) | 90 | 60 | 5 | 58 | 88 | 3.26 | 98 | 3.45 |

Comparative Example 1

Immobilization of Butylamino Group (Secondary Amino Group and Butyl Group) on Graft Chain:

The hollow fiber porous membrane having graft chains introduced obtained in (i) of Production Example 1 was swollen by immersion in methanol for 10 minutes or more, and subjected to water replacement by immersion in pure water. To 92.7 parts by weight of purified water was added 7.3 parts by weight of normal butylamine, which was then stirred and dissolved to prepare a reaction solution. In a glass reaction tube was then placed 25 parts by mass of the reaction solution based on the dry weight of the hollow fiber porous membrane having graft chains introduced obtained in (i) above, which was adjusted at 40° C. Thereafter, the hollow fiber porous membrane having graft chains introduced, after immersion in pure water was inserted into the reaction solution and allowed to stand for 20 hours to replace epoxy groups on the graft chains with butylamino groups to provide a hollow fiber porous membrane having secondary amino groups and butyl groups immobilized via the graft chains. The resultant hollow fiber porous membrane had an outer diameter of 3.49 mm and an inner diameter of 2.16 mm; from the equation (2), 79% of all of the epoxy groups which the graft chains had were found to be replaced by butylamino groups.

Using the hollow fiber porous membrane having butylamino groups, a hollow fiber porous membrane module was chloride concentration of 0 mole/L was again determined according to Evaluation Method Example 2, the value of 9 mg/mL which was lower than for the first determination was obtained. Thus, the hollow fiber porous membrane module according to Comparative Example 1 could not be properly washed or regenerated with a solution containing a high concentration of a salt.

The recovery rate and the dimer ratio after passing an antibody protein solution were also evaluated according to Evaluation Method Example 2. The recovery rate of the antibody was 92% for the sodium chloride concentration of 0 mole/L and 97% for the sodium chloride concentration of 0.1 mole/L. The dimer ratio was 3.02% for the sodium chloride concentration of 0 mole/L and 3.32% for the sodium chloride concentration of 0.1 mole/L, showing that this result was inferior to that of Example 1. These results are shown in Table 1.

Example 2

Immobilization of Propylamino Group (Secondary Amino Group and Propyl Group) on Graft Chain The hollow fiber porous membrane having graft chains introduced obtained in (i) of Production Example 1 was swollen by immersion in methanol for 10 minutes or more, and subjected to water replacement by immersion in pure water. Normal propylamine was added to 20 mL of purified water while stirring to a total volume of 40 mL to prepare a reaction solution. In a glass reaction tube was then placed 25 parts by mass of the reaction solution based on the dry weight of the hollow fiber porous membrane having graft chains introduced obtained in (i) above, which was adjusted at 40° C. Thereafter, the hollow fiber porous membrane having graft chains introduced, after immersion in pure water was inserted into the reaction solution and allowed to stand for 24 hours to replace epoxy groups on the graft chains with propylamino groups to provide a hollow fiber porous membrane having secondary amino groups and propyl groups immobilized via the graft chains. The resultant hollow fiber porous membrane had an outer diameter of 3.44 mm and an inner diameter of 2.10 mm; from the equation (2), 78% of the total epoxy groups which the graft chains had were found to be replaced by propylamino groups.

Using the hollow fiber porous membrane having propylamino groups, a hollow fiber porous membrane module was then prepared according to (iii) of Production Example 1. The volume of only the hollow fiber porous membrane in the hollow fiber porous membrane module, in which the hollow parts of the membrane are removed was 0.54 mL. The inner surface area of the hollow fiber porous membrane was 6.1 cm². When the BSA dynamic adsorption volume was determined according to Evaluation Method Example 2 using the resultant hollow fiber porous membrane module, it was 49 mg/mL and 21 mg/mL for the sodium chloride concentrations of 0 mole/L and 0.1 mole/L, respectively.

In addition, 20 mL of a 20 mmole Tris-HCl (pH 8.0) solution containing 1 mole/L NaCl was further passed through the hollow fiber porous membrane module after evaluating the adsorption of BSA for 0 mole/L to elute the adsorbed BSA. Thereafter, when the BSA dynamic adsorption volume of the hollow fiber porous membrane module for the sodium chloride concentration of 0 mole/L was again determined according to Evaluation Method Example 2, almost the same value of 47 mg/mL was obtained. Thus, the present hollow fiber porous membrane module could be properly washed and regenerated with a solution containing a high concentration of a salt.

The recovery rate and the dimer ratio after passing an antibody protein solution were also evaluated according to Evaluation Method Example 2. The recovery rate of the antibody was 90% for the sodium chloride concentration of 0 mole/L and 95% for the sodium chloride concentration of 0.1 mole/L. The dimer ratio was 1.08% for the sodium chloride concentration of 0 mole/L and 1.24% for the sodium chloride concentration of 0.1 mole/L. These results are shown in Table 1.

Example 3

Immobilization of Diethylamino Group (Tertiary Amino Group and Diethylamino Group) on Graft Chain The hollow fiber porous membrane having graft chains introduced obtained in (i) of Production Example 1 was swollen by immersion in methanol for 10 minutes or more, and subjected to water replacement by immersion in pure water. Diethylamine was added to 20 mL of purified water while stirring to a total volume of 40 mL to prepare a reaction solution. In a glass reaction tube was then placed 25 parts by mass of the reaction solution based on the dry weight of the hollow fiber porous membrane after introducing graft chains obtained in (i) above, which was adjusted at 30° C. Thereafter, the hollow fiber porous membrane having graft chains introduced, after immersion in pure water was inserted into the reaction solution and allowed to stand for 24 hours to replace epoxy groups on the graft chains with diethylamino groups to provide a hollow fiber porous membrane having tertiary amino groups and ethyl groups immobilized via the graft chains. The resultant hollow fiber porous membrane had an outer diameter of 3.54 mm and an inner diameter of 2.17 mm; from the equation (2), 89% of the total epoxy groups which the graft chains had were found to be replaced by diethylamino groups.

Using the hollow fiber porous membrane having diethylamino groups, a hollow fiber porous membrane module was then prepared according to (iii) of Production Example 1. The volume of only the hollow fiber porous membrane in the hollow fiber porous membrane module, in which the hollow parts of the membrane are removed was 0.56 mL. The inner surface area of the hollow fiber porous membrane was 6.3 cm². When the BSA dynamic adsorption volume was determined according to Evaluation Method Example 2 using the resultant hollow fiber porous membrane module, it was 59 mg/mL and 24 mg/mL for the sodium chloride concentrations of 0 mole/L and 0.1 mole/L, respectively.

In addition, 20 mL of a 20 mmole Tris-HCl (pH 8.0) solution containing 1 mole/L NaCl was passed through the hollow fiber porous membrane module after evaluating the adsorption of BSA for 0 mole/L to elute the adsorbed BSA. Thereafter, when the BSA dynamic adsorption volume of the hollow fiber porous membrane module for the sodium chloride concentration of 0 mole/L was again determined according to Evaluation Method Example 2, almost the same value of 58 mg/mL was obtained. Thus, the present hollow fiber porous membrane module could be properly washed and regenerated with a solution containing a high concentration of a salt.

The recovery rate and the dimer ratio after passing an antibody protein solution were also evaluated according to Evaluation Method Example 2. The recovery rate of the antibody was 91% for the sodium chloride concentration of 0 mole/L and 96% for the sodium chloride concentration of 0.1 mole/L. The dimer ratio was 0.83% for the sodium chloride concentration of 0 mole/L and 0.91% for the sodium chloride concentration of 0.1 mole/L. These results are shown in Table 1.

Comparative Example 2

Immobilization of Dimethylamino Group (Tertiary Amino Group and Methyl Group) on Graft Chain The hollow fiber porous membrane having graft chains introduced obtained in (i) of Production Example 1 was swollen by immersion in methanol for 10 minutes or more, and subjected to water replacement by immersion in pure water. Dimethylamine was added to 25 mL of purified water while stirring to a total volume of 40 mL to prepare a reaction solution. In a glass reaction tube was then placed 25 parts by mass of the reaction solution based on the dry weight of the hollow fiber porous membrane after introducing graft chains obtained in (i) above, which was adjusted at 30° C. Thereafter, the hollow fiber porous membrane having graft chains introduced, after immersion in pure water was inserted into the reaction solution and allowed to stand for 48 hours to replace epoxy groups on the graft chains with dimethylamino groups to provide a hollow fiber porous membrane having tertiary amino groups and methyl groups immobilized via the graft chains. The resultant hollow fiber porous membrane had an outer diameter of 3.40 mm and an inner diameter of 2.07 mm; from the equation (2), 69% of all of the epoxy groups which the graft chains had were found to be replaced by dimethylamino groups.

Using the hollow fiber porous membrane having diethylamino groups, a hollow fiber porous membrane module was then prepared according to (iii) of Production Example 1. The volume of only the hollow fiber porous membrane in the hollow fiber porous membrane module, in which the hollow parts of the membrane are removed was 0.53 mL. The inner surface area of the hollow fiber porous membrane was 6.0 cm$^2$. When the BSA dynamic adsorption volume was determined according to Evaluation Method Example 2 using the resultant hollow fiber porous membrane module, it was 22 mg/mL and 11 mg/mL for the sodium chloride concentrations of 0 mole/L and 0.1 mole/L, respectively, showing decreased dynamic adsorption volumes.

In addition, 20 mL of a 20 mmole Tris-HCl (pH 8.0) solution containing 1 mole/L NaCl was further passed through the hollow fiber porous membrane module after evaluating the adsorption of BSA for 0 mole/L to elute the adsorbed BSA. Thereafter, when the BSA dynamic adsorption volume of the hollow fiber porous membrane module for the sodium chloride concentration of 0 mole/L was again determined according to Evaluation Method Example 2, almost the same value of 21 mg/mL was obtained. Therefore, the present hollow fiber porous membrane module according to Comparative Example 2 could be properly washed and regenerated with a solution containing a high concentration of a salt, but had a decreased BSA dynamic adsorption volume.

The recovery rate and the dimer ratio after passing an antibody protein solution were also evaluated according to Evaluation Method Example 2. The recovery rate of the antibody was 93% for the sodium chloride concentration of 0 mole/L and 97% for the sodium chloride concentration of 0.1 mole/L. The dimer ratio was 3.13% for the sodium chloride concentration of 0 mole/L and 3.65% for the sodium chloride concentration of 0.1 mole/L. These results are shown in Table 1.

Comparative Example 3

Immobilization of Dipropylamino Group (Tertiary Amino Group and Propyl Group) on Graft Chain The hollow fiber porous membrane having graft chains introduced obtained in (i) of Production Example 1 was swollen by immersion in methanol for 10 minutes or more, and subjected to water replacement by immersion in pure water. After mixing and stirring 5 mL of purified water and 20 mL of isopropyl alcohol, dipropylamine was added thereto while stirring to a total volume of 40 mL to prepare a reaction solution. In a glass reaction tube was then placed 25 parts by mass of the reaction solution based on the dry weight of the hollow fiber porous membrane after introducing graft chains obtained in (i) above, which was adjusted at 30° C. Thereafter, the hollow fiber porous membrane having graft chains introduced, after immersion in pure water was inserted into the reaction solution and allowed to stand for 48 hours to replace epoxy groups on the graft chains with dipropylamino groups to provide a hollow fiber porous membrane having tertiary amino groups and propyl groups immobilized via the graft chains. The resultant hollow fiber porous membrane had an outer diameter of 3.46 mm and an inner diameter of 2.11 mm; from the equation (2), 68% of all of the epoxy groups which the graft chains had were found to be replaced by dipropylamino groups.

Using the hollow fiber porous membrane having dipropylamino groups, a hollow fiber porous membrane module was then prepared according to (iii) of Production Example 1. The volume of only the hollow fiber porous membrane in the hollow fiber porous membrane module, in which the hollow parts of the membrane are removed was 0.54 mL. The inner surface area of the hollow fiber porous membrane was 6.1 cm$^2$. When the BSA dynamic adsorption volume was determined according to Evaluation Method Example 2 using the resultant hollow fiber porous membrane module, it was 16 mg/mL and 7 mg/mL for the sodium chloride concentrations of 0 mole/L and 0.1 mole/L, respectively, showing decreased dynamic adsorption volumes.

In addition, 20 mL of a 20 mmole Tris-HCl (pH 8.0) solution containing 1 mole/L NaCl was passed through the hollow fiber porous membrane module after evaluating the adsorption of BSA for 0 mole/L to elute the adsorbed BSA. Thereafter, when the BSA dynamic adsorption volume of the hollow fiber porous membrane module for the sodium chloride concentration of 0 mole/L was again determined according to Evaluation Method Example 2, the value of 10 mg/mL which was lower than for the first determination was obtained. Therefore, the present hollow fiber porous membrane module according to Comparative Example 3 could not be properly washed or regenerated with a solution containing a high concentration of a salt.

The recovery rate and the dimer ratio after passing an antibody protein solution were also evaluated according to Evaluation Method Example 2. The recovery rate of the antibody was 94% for the sodium chloride concentration of 0 mole/L and 98% for the sodium chloride concentration of 0.1 mole/L. The dimer ratio was 3.21% for the sodium chloride concentration of 0 mole/L and 3.54% for the sodium chloride concentration of 0.1 mole/L. These results are shown in Table 1.

Example 4

Immobilization of Triethylamino Group (Quaternary Amino Group and Ethyl Group) on Graft Chain The hollow fiber porous membrane having graft chains introduced obtained in (i) of Production Example 1 was swollen by immersion in methanol for 10 minutes or more, and subjected to water replacement by immersion in pure water. A 1 mole/L NaOH aqueous solution (17 mL) and methanol (17 mL) were mixed and stirred, to which triethylamine hydrochloride (4.81 g) was added while stirring to prepare a reaction solution. In a glass reaction tube was then placed 25 parts by mass of the reaction solution based on the dry weight of the hollow fiber porous membrane after introducing graft chains obtained in (i) above, which was adjusted at 40° C. Thereafter, the hollow fiber porous membrane having graft chains introduced, after immersion in pure water was inserted into the prepared reaction solution and allowed to stand for 36 hours to replace epoxy groups on the graft chains with triethylamino groups to provide a hollow fiber porous membrane having quaternary amino groups and ethyl groups immobilized via the graft chains. The resultant hollow fiber porous membrane had an outer diameter of 3.51 mm and an inner diameter of 2.13 mm; from the equation (2), 69% of all of the epoxy groups which the graft chains had were found to be replaced by triethylamino groups.

Using the hollow fiber porous membrane having triethylamino groups, a hollow fiber porous membrane module was then prepared according to (iii) of Production Example 1. The volume of only the hollow fiber porous membrane in the hollow fiber porous membrane module, in which the hollow parts of the membrane are removed was 0.56 mL. The inner surface area of the hollow fiber porous membrane was 6.2 cm$^2$. When the BSA dynamic adsorption volume was determined according to Evaluation Method Example 2 using the resultant hollow fiber porous membrane module, it was 67 mg/mL and 31 mg/mL for the sodium chloride concentrations of 0 mole/L and 0.1 mole/L, respectively.

In addition, 20 mL of a 20 mmole Tris-HCl (pH 8.0) solution containing 1 mole/L NaCl was passed through the hollow fiber porous membrane module after evaluating the adsorption of BSA for 0 mole/L to elute the adsorbed BSA. Thereafter, when the BSA dynamic adsorption volume of the hollow fiber porous membrane module for the sodium chloride concentration of 0 mole/L was again determined according to Evaluation Method Example 2, almost the same value of 65 mg/mL was obtained. Thus, the hollow fiber porous membrane module according to Example 4 could be properly washed and regenerated with a solution containing a salt.

The recovery rate and the dimer ratio after passing an antibody protein solution were also evaluated according to Evaluation Method Example 2. The recovery rate of the antibody was 92% for the sodium chloride concentration of 0 mole/L and 97% for the sodium chloride concentration of 0.1 mole/L. The dimer ratio was 0.71% for the sodium chloride concentration of 0 mole/L and 0.78% for the sodium chloride concentration of 0.1 mole/L. These results are shown in Table 1.

Example 5

Immobilization of Tripropylamino Group
(Quaternary Amino Group and Propyl Group) on
Graft Chain The hollow fiber porous membrane having graft chains introduced obtained in (i) of Production Example 1 was swollen by immersion in methanol for 10 minutes or more, and subjected to water replacement by immersion in pure water. Methanol (17 mL), purified water (7.5 mL) and sodium hydroxide (0.84 g) were mixed and stirred, to which 4.71 g of tripropylamine hydrochloride was added while stirring to prepare a reaction solution. In a glass reaction tube was then placed 25 parts by mass of the reaction solution based on the dry weight of the hollow fiber porous membrane after introducing graft chains obtained in (i) above, which was adjusted at 40° C. Thereafter, the hollow fiber porous membrane having graft chains introduced, after immersion in pure water was inserted into the prepared reaction solution and allowed to stand for 46 hours to replace epoxy groups on the graft chains with tripropylamino groups to provide a hollow fiber porous membrane having quaternary amino groups and propyl groups immobilized via the graft chains. The resultant hollow fiber porous membrane had an outer diameter of 3.43 mm and an inner diameter of 2.09 mm; from the equation (2), 63% of all of the epoxy groups which the graft chains had were found to be replaced by tripropylamino groups.

Using the hollow fiber porous membrane having tripropylamino groups, a hollow fiber porous membrane module was then prepared according to (iii) of Production Example 1. The volume of only the hollow fiber porous membrane in the hollow fiber porous membrane module, in which the hollow parts of the membrane are removed was 0.53 mL. The inner surface area of the hollow fiber porous membrane was 6.0 cm$^2$. When the BSA dynamic adsorption volume was determined according to Evaluation Method Example 2 using the resultant hollow fiber porous membrane module, it was 53 mg/mL and 27 mg/mL for the sodium chloride concentrations of 0 mole/L and 0.1 mole/L, respectively.

In addition, 20 mL of a 20 mmole Tris-HCl (pH 8.0) solution containing 1 mole/L NaCl was passed through the hollow fiber porous membrane module after evaluating the adsorption of BSA for 0 mole/L to elute the adsorbed BSA. Thereafter, when the BSA dynamic adsorption volume of the hollow fiber porous membrane module for the sodium chloride concentration of 0 mole/L was again determined according to Evaluation Method Example 2, almost the same value of 50 mg/mL was obtained. Thus, the hollow fiber porous membrane module according to Example 5 could be properly washed and regenerated with a solution containing a salt.

The recovery rate and the dimer ratio after passing an antibody protein solution were also evaluated according to Evaluation Method Example 2. The recovery rate of the antibody was 89% for the sodium chloride concentration of 0 mole/L and 96% for the sodium chloride concentration of 0.1 mole/L. The dimer ratio was 1.05% for the sodium chloride concentration of 0 mole/L and 1.23% for the sodium chloride concentration of 0.1 mole/L. These results are shown in Table 1.

Comparative Example 4

Immobilization of Trimethylamino Group
(Quaternary Amino Group and Methyl Group) on
Graft Chain The hollow fiber porous membrane having graft chains introduced obtained in (i) of Production Example 1 was swollen by immersion in methanol for 10 minutes or more, and subjected to water replacement by immersion in pure water. Purified water (12.5 mL) and a 1 mole/L NaOH aqueous solution (12.5 mL) were mixed and stirred, to which 1.19 g of trimethylamine hydrochloride was added to prepare a reaction solution. In a glass reaction tube was then placed 25 parts by mass of the reaction solution based on the dry weight of the hollow fiber porous membrane after introducing graft chains obtained in (i) above, which was adjusted at 40° C. Thereafter, the hollow fiber porous membrane having graft chains introduced, after immersion in pure water was inserted into the prepared reaction solution and allowed to stand for 6 hours to replace epoxy groups on the graft chains with trimethylamino groups to provide a hollow fiber porous membrane having quaternary amino groups and methyl groups immobilized via the graft chains. The resultant hollow fiber porous membrane had an outer diameter of 3.53 mm and an inner diameter of 2.15 mm; from the equation (2), 90% of all of the epoxy groups which the graft chains had were found to be replaced by trimethylamino groups.

Using the hollow fiber porous membrane having trimethylamino groups, a hollow fiber porous membrane module was prepared according to (iii) of Production Example 1. The volume of only the hollow fiber porous membrane in the hollow fiber porous membrane module, in which the hollow parts of the membrane are removed was 0.56 mL. The inner surface area of the hollow fiber porous membrane was 6.2 cm$^2$. When the BSA dynamic adsorption volume was determined according to Evaluation Method Example 2 using the resultant hollow fiber porous membrane module, it was 60 mg/mL for the sodium chloride concentration of 0 mole/L but was as low as 6 mg/mL for the sodium chloride concentration of 0.1 mole/L.

In addition, 20 mL of a 20 mmole Tris-HCl (pH 8.0) solution containing 1 mole/L NaCl was passed through the hollow fiber porous membrane module after evaluating the adsorption of BSA for 0 mole/L to elute the adsorbed BSA. Further, when the BSA dynamic adsorption volume of the hollow fiber porous membrane module for 0 mole/L sodium chloride was again determined according to Evaluation Method Example 2, almost the same value of 58 mg/mL was obtained. Thus, the hollow fiber porous membrane module according to Comparative Example 4 could be properly washed and regenerated with a solution containing a salt but was found to be inferior in the protein adsorbing capacity for a solution having a high salt concentration.

The recovery rate and the dimer ratio after passing an antibody protein solution were also evaluated according to Evaluation Method Example 2. The recovery rate of the antibody was 88% for the sodium chloride concentration of 0 mole/L and 98% for the sodium chloride concentration of 0.1 mole/L. The dimer ratio was 3.26% for the sodium chloride concentration of 0 mole/L and 3.45% for the sodium chloride concentration of 0.1 mole/L. These results are shown in Table 1.

on the volume of the membrane contained in the hollow fiber porous membrane module was continuously collected in the form of fractions. The antibody protein recovery rate based on the amount of the passed solution and the concentration of impurities in each passed fraction were measured. The results are shown in Table 2. As shown in Table 2, the impurities in the solution passed through the hollow fiber porous membrane module were considerably decreased compared to those in the feed solution. When the volume of the passed solution exceeded 40 times the membrane volume, the recovery rate of the antibody protein reached 90% or more. In addition, the ratio of the monomer and the aggregates of the antibody protein contained in each passed fraction were evaluated by the method described in Evaluation Method Example 3 to determine the ratio of a dimer in the antibody protein. The results are also shown in Table 2. As shown in Table 2, the dimer of the antibody protein in the solution passed through the hollow fiber porous membrane module was significantly decreased compared to that in the feed solution.

TABLE 2

| | Ligand Species | Evaluation Item | Feed Stock Solution | Passage Amount of Each Fraction MV: Membrane Volume | | | | |
|---|---|---|---|---|---|---|---|---|
| | | | | 20 MV | 40 MV | 60 MV | 80 MV | 100 MV |
| Example 7 | IPA | Antibody Recovery Rate | | 84% | 91% | 93% | 94% | 96% |
| | | Impurity | 100 ug/mL | 7.8 ug/mL | 10.9 ug/mL | 11.3 ug/mL | 12.5 ug/mL | 13.1 ug/mL |
| | | HCP | 87 ug/mL | 6.9 ug/mL | 8.7 ug/mL | 9.5 ug/mL | 10.2 ug/mL | 11.1 ug/mL |
| | | DNA | 1.7 ug/mL | 18.9 ng/mL | 18.5 ng/mL | 18.4 ng/mL | 18.3 ng/mL | 18.4 ng/mL |
| | | Dimer Ratio | 4.06% | 0.10% | 0.54% | 0.89% | 1.09% | 1.27% |
| Example 8 | PA | Antibody Recovery Rate | | 82% | 90% | 93% | 95% | 97% |
| | | Impurity | 100 ug/mL | 9.1 ug/mL | 11.4 ug/mL | 12.4 ug/mL | 13.1 ug/mL | 15.3 ug/mL |
| | | HCP | 87 ug/mL | 7.4 ug/mL | 9.5 ug/mL | 10.2 ug/mL | 11.3 ug/mL | 12.8 ug/mL |
| | | DNA | 1.7 ug/mL | 19.6 ng/mL | 18.7 ng/mL | 18.9 ng/mL | 19.1 ng/mL | 18.9 ng/mL |
| | | Dimer Ratio | 4.06% | 0.11% | 0.56% | 0.97% | 1.12% | 1.35% |
| Example 9 | DEA | Antibody Recovery Rate | | 85% | 92% | 93% | 95% | 97% |
| | | Impurity | 100 ug/mL | 14.7 ug/mL | 20.6 ug/mL | 23.2 ug/mL | 24.9 ug/mL | 26 ug/mL |
| | | HCP | 87 ug/mL | 13.1 ug/mL | 16.2 ug/mL | 18.2 ug/mL | 19.3 ug/mL | 19.9 ug/mL |
| | | DNA | 1.7 ug/mL | 20.4 ng/mL | 18.2 ng/mL | 19 ng/mL | 19.3 ng/mL | 18.4 ng/mL |
| | | Dimer Ratio | 4.06% | 0.08% | 0.43% | 0.62% | 0.86% | 0.98% |
| Example 10 | TEA | Antibody Recovery Rate | | 87% | 93% | 95% | 95% | 98% |
| | | Impurity | 100 ug/mL | 13.7 ug/mL | 19.9 ug/mL | 22.1 ug/mL | 23.8 ug/mL | 25.4 ug/mL |
| | | HCP | 87 ug/mL | 11.5 ug/mL | 13.2 ug/mL | 14.6 ug/mL | 15.4 ug/mL | 16.9 ug/mL |
| | | DNA | 1.7 ug/mL | 18.4 ng/mL | 18.2 ng/mL | 19.2 ng/mL | 19.1 ng/mL | 18.9 ng/mL |
| | | Dimer Ratio | 4.06% | 0.00% | 0.32% | 0.45% | 0.63% | 0.83% |
| Comparative Example 5 | TMA | Antibody Recovery Rate | | 86% | 93% | 94% | 95% | 98% |
| | | Impurity | 100 ug/mL | 43.8 ug/mL | 48.5 ug/mL | 53.2 ug/mL | 55.6 ug/mL | 58.9 ug/mL |
| | | HCP | 87 ug/mL | 39.8 ug/mL | 42.3 ug/mL | 46.5 ug/mL | 49.3 ug/mL | 51.9 ug/mL |
| | | DNA | 1.7 ug/mL | 19.4 ng/mL | 18.7 ng/mL | 20.1 ng/mL | 21.3 ng/mL | 21.2 ng/mL |
| | | Dimer Ratio | 4.06% | 1.08% | 3.13% | 3.57% | 3.82% | 3.88% |

Example 7

Purification of Antibody Solution Using Porous Membrane Having Isopropylamino Group The feed solution composed of impurities consisting mainly of HCP and an antibody protein prepared in Evaluation Method Example 3 was passed through the hollow fiber porous membrane module prepared in Example 1. In addition, the passed solution equivalent to 20 volume based Example 8

Purification of Antibody Solution Using Porous Membrane Having Propylamino Group The feed solution composed of impurities consisting mainly of HCP and an antibody protein prepared in Evaluation Method Example 3 was passed through the hollow fiber porous membrane module prepared in Example 2. In addition, the passed solution equivalent to 20 volume based on the volume of the membrane contained in the hollow fiber porous membrane module was continuously collected in the form of fractions. The antibody protein recovery rate based on the amount of the passed solution and the concentration of impurities in each passed fraction were measured. The results are shown in Table 2. As shown in Table 2, the impurities in the solution passed through the hollow fiber porous membrane module were considerably decreased compared to those in the feed solution. When the volume of the passed solution exceeded 40 times the membrane volume, the recovery rate of the antibody protein reached 90% or more. In addition, the ratio of the monomer and the aggregates of the antibody protein contained in each passed fraction were evaluated by the method described in Evaluation Method Example 3 to determine the ratio of a dimer in the antibody protein. The results are also shown in Table 2. As shown in Table 2, the dimer of the antibody protein in the solution passed through the hollow fiber porous membrane module was significantly decreased compared to that in the feed solution.

Example 9

Purification of Antibody Solution Using Porous Membrane Having Diethylamino Group The feed solution composed of impurities consisting mainly of HCP and an antibody protein prepared in Evaluation Method Example 3 was passed through the hollow fiber porous membrane module prepared in Example 3. In addition, the passed solution equivalent to 20 volume based on the volume of the membrane contained in the hollow fiber porous membrane module was continuously collected in the form of fractions. The antibody protein recovery rate based on the amount of the passed solution and the concentration of impurities in each passed fraction were measured. The results are shown in Table 2. As shown in Table 2, the impurities in the solution passed through the hollow fiber porous membrane module were considerably decreased compared to those in the feed solution. When the volume of the passed solution exceeded 40 times the membrane volume, the recovery rate of the antibody protein reached 90% or more. In addition, the ratio of the monomer and the aggregates of the antibody protein contained in each passed fraction were evaluated by the method described in Evaluation Method Example 3 to determine the ratio of a dimer in the antibody protein. The results are also shown in Table 2. As shown in Table 2, the dimer of the antibody protein in the solution passed through the hollow fiber porous membrane module was significantly decreased compared to that in the feed solution.

Example 10

Purification of Antibody Solution Using Porous Membrane Having Triethylamino Group The feed solution composed of impurities consisting mainly of HCP and an antibody protein prepared in Evaluation Method Example 3 was passed through the hollow fiber porous membrane module prepared in Example 4. In addition, the passed solution equivalent to 20 volume based on the volume of the membrane contained in the hollow fiber porous membrane module was continuously collected in the form of fractions. The antibody protein recovery rate based on the amount of the passed solution and the concentration of impurities in each passed fraction were measured. The results are shown in Table 2. As shown in Table 2, the impurities in the solution passed through the hollow fiber porous membrane module were considerably decreased compared to those in the feed solution. When the volume of the passed solution exceeded 40 times the membrane volume, the recovery rate of the antibody protein reached 90% or more. In addition, the ratio of the monomer and the aggregates of the antibody protein contained in each passed fraction were evaluated by the method described in Evaluation Method Example 3 to determine the ratio of a dimer in the antibody protein. The results are also shown in Table 2. As shown in Table 2, the dimer of the antibody protein in the solution passed through the hollow fiber porous membrane module was considerably decreased compared to that in the feed solution.

Comparative Example 5

Purification of Antibody Solution Using Porous Membrane Having Trimethylamino Group The feed solution composed of impurities consisting mainly of HCP and an antibody protein prepared in Evaluation Method Example 3 was passed through the hollow fiber porous membrane module prepared in Comparative Example 4. In addition, the passed solution equivalent to 20 volume based on the volume of the membrane contained in the hollow fiber porous membrane module was continuously collected in the form of fractions. The antibody protein recovery rate based on the amount of the passed solution and the concentration of impurities in each passed fraction were measured. The results are shown in Table 2. Table 2 showed that when the volume of the passed solution exceeded 40 times the membrane volume, the recovery rate of the antibody protein reached 90% or more, but the impurities in the solution passed through the hollow fiber porous membrane module according to Comparative Example were decreased only by about half compared to those in the feed solution. The ratio of the monomer and the aggregates of the antibody protein contained in each passed fraction were also evaluated by the method described in Evaluation Method Example 3 to determine the ratio of a dimer in the antibody protein. The results are also shown in Table 2. Table 2 showed that the extent of the decrease of the dimer of the antibody protein in the hollow fiber porous membrane module according to Comparative Example was limited.

As described above, provided are a porous membrane comprising a hydrophobic porous substrate, a hydrophilic molecular chain of a different material from that of the porous substrate, immobilized on the surface containing pores of the porous substrate, and a side chain containing a nitrogen atom to which one to three alkyl groups each having two or three carbon atoms are bonded, a hydroxyl group, and a carbonyl group, and a method for producing the same. In addition, we have found that the porous membrane was used to remove, by adsorption, impurities from an antibody solution in a practical salt concentration to thereby simply purify the antibody with rapidity.

The present application is based on Japanese Patent Application No. 2009-158421 filed in the Japanese Patent Office Jul. 3, 2009, the contents of which are incorporated herein by reference.

INDUSTRIAL APPLICABILITY

The method according to the present embodiment enables rapid and highly efficient treatment compared to a conventional method using column chromatography and can be easily scaled up. From this, the present method has an industrial applicability that it is suitable for the purification of an antibody in producing a pharmaceutical preparation at an industrial level.

The invention claimed is:

1. A method for purifying an antibody monomer, comprising:
   passing an antibody solution containing antibody aggregates of dimers or higher-order multimers through a porous membrane to adsorb the antibody aggregates to the porous membrane, the porous membrane comprising
   a hydrophobic porous substrate,
   a hydrophilic molecular chain of a different material from that of the porous substrate, the hydrophilic molecular chain being immobilized on the surface of pores of the porous substrate, and
   a side chain of the hydrophilic molecular chain containing a nitrogen atom to which one or three alkyl side chains each having two or three carbon atoms are bonded; and
   recovering the purified antibody monomer in the passed solution;
   wherein the nitrogen atom is contained in an amino group, and the amino group that contains the nitrogen atom is a monoalkyl-substituted amino group or a trialkyl-substituted amino group.

2. The method for purifying an antibody monomer according to claim 1, wherein the antibody solution further contains at least one contaminant selected from a host cell protein, a deoxyribonucleic acid, an endotoxin, a protease, and a virus.

3. The method for purifying an antibody monomer according to claim 1, wherein:
   the antibody solution has a salt concentration of 0.3 mol/L or less; and
   the side chain further contains a hydroxyl group and a carbonyl group.

4. The method for purifying an antibody monomer according to claim 1, wherein:
   the side chain contains at least one amino group selected from a propylamino group, an isopropylamino group, a triethylamino group, and a tripropylamino group;
   the antibody solution further contains at least one impurity selected from an impurity protein, a host cell protein, a deoxyribonucleic acid, an endotoxin, a protease, and a virus;
   the recovery rate of the antibody monomer is 80% or more; and
   the method further comprises, after passing the antibody solution through the porous membrane, eluting impurities adsorbed to the porous membrane by passing a 40 mS/cm or more of a solution through the porous membrane to enable the reuse of the porous membrane.

5. The method for purifying an antibody monomer according to claim 1, wherein the porous substrate comprises at least one selected from polyethylene, polypropylene, polysulfone, polyether sulfone, and polyvinylidene fluoride.

6. The method for purifying an antibody monomer according to claim 1, wherein the backbone of the molecular chain is a polymer of at least one monomer selected from glycidyl methacrylate, glycidyl acrylate, glycidyl sorbate, glycidyl itacolate, and glycidyl maleate.

7. The method for purifying an antibody monomer according to claim 1, wherein one nitrogen atom-containing functional group selected from a propylamino group, an isopropylamino group, a triethylamino group, and a tripropylamino group is bonded to 60% to 97% (both inclusive) of all of the side chains held by the molecular chain.

* * * * *